United States Patent [19]

Romeo et al.

[11] Patent Number: 5,556,843
[45] Date of Patent: Sep. 17, 1996

[54] THERAPEUTIC USE OF PHOSPHORYL-L-SERINE-N-ACYL-SPHINGOSINE

[75] Inventors: Aurelio Romeo, Rome; Gunter Kirschner, Abano Terme; Gianpaolo Menon, Battaglia Terme, all of Italy

[73] Assignee: Fidia, S.p.A., Abano Terme, Italy

[21] Appl. No.: 374,624

[22] PCT Filed: Aug. 2, 1993

[86] PCT No.: PCT/EP93/02061

§ 371 Date: Mar. 9, 1995

§ 102(e) Date: Mar. 9, 1995

[87] PCT Pub. No.: WO94/03178

PCT Pub. Date: Feb. 17, 1994

[30] Foreign Application Priority Data

Aug. 3, 1992 [IT] Italy .................. PD92A0145

[51] Int. Cl.$^6$ ........................... A61K 31/66
[52] U.S. Cl. .................................... 514/114
[58] Field of Search ............................ 514/114

[56] References Cited

PUBLICATIONS

JP 1135720 Abstract (Derwent) 29 May 1989.

*Primary Examiner*—Phyllis G. Spivack
*Attorney, Agent, or Firm*—Birch, Stewart, Kolasch & Birch, LLP

[57] ABSTRACT

The present invention relates to a therapeutic use of phosphoryl-L-serine-N-acyl-sphingosine comprising a mixture of compounds of instant formula I or II that are herein disclosed.

8 Claims, No Drawings

THERAPEUTIC USE OF PHOSPHORYL-L-SERINE-N-ACYL-SPHINGOSINE

This application is a 371 of PCT/EP 93/02061, filed Aug. 2, 1993.

BACKGROUND AND SUMMARY OF THE INVENTION

The present invention concerns the therapeutic use of phosphoryl-L-serine-N-acyl-sphingosine composed of a mixture of compounds of formula I or II,

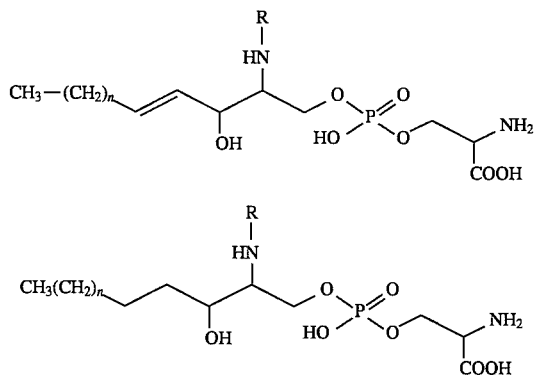

in which n is an integer of 6–16 and R means an acyl residue of a higher aliphatic acid having between 16 and 24 carbon atoms, the distribution of the values for n and R being those of a natural spingomyelin. The invention also includes a new process for the preparation of these compounds, as well as pharmaceutical preparations containing said compounds as active ingredients. The ratio of the mixture of compounds of formulas (I) and (II) is not critical in order to use the compound of the present invention. The compound, as previously defined, was prepared by treatment with phospholipase D, as described in Biochemistry vol. 28, No. 8, 1989, 34–57, starting from a derivative of spingomyelin (i.e. phosphorylcholine-N-acyl-sphingosine, in which the acyl group was derived from higher aliphatic acids of different molecular size and was variable between C12 and C24), and particularly to an analog of a spingomyelin having an acyl group derived from 4-doxyl-pentanoic acid on the sphingosine amino group instead of the acyl residue R. In the cited paper there are no indications about pharmacological properties of the derivatives.

DETAILED DESCRIPTION OF THE INVENTION

It has now been found that the compound has various interesting pharmacological properties and can be used therapeutically, especially in human medicine. More precisely the phosphoryl-L-serine-N-acyl-sphinogosine of the present invention has an inhibiting action on the activation of protein kinase C, which, activation can be undesired or have negative effect, in particular conditions of unbalance of the normal mechanisms of neurotransmittal functions. Activation is caused by an increased concentration of excitatory amino acids, like glutamic and/or aspartic acid; these acids have a direct toxic action on neuronal cells in the above mentioned abnormal conditions.

Phosphoryl-L-serine-N-acyl-spingosine can therefore be used in the therapy of many diseases of the central nervous system, as those arising after cerebral degenerations or lesions, like ischaemia, hypoxia, epilepsy, traumas and compressions, metabolic dysfunctions, aging, toxic-infective and chronic degenerative diseases, like Alzheimer's, Parkinson's and Huntington's diseases.

Phosphoryl-L-serine-N-acyl-sphingosine is moreover able to increase glycemia and histamine levels, resulting in cerebral glucose accumulation, which has important reflexes in the functionality of CNS. Also an activating influence on cerebral neurotransmitter systems was shown, particularly at the cholinergic level, the compounds of the present invention can increase the release of acetylcoline (ACh) in the cerebral cortex area. The action on the cholinergic system is also reinforced by the efficacy of the aforesaid compounds in influencing cognitive functions, like e.g. learning and memorizing, in various behavioral tests (e.g. the capacity to invert scopolamine caused amnesia). The compounds I and II can also be used in therapies associated with slowdown of cerebral metabolism, in involutive cerebral syndromes of different origins (due e.g. to senile decay and/or vascular pathologies), in Alzheimer's disease, memory loss and senile dementia, anoxic and edematous conditions, cerebral tiredness, chronic vascular cerebropathies of aging, and pre-senile dementia following trauma, postanoxic cerebropathies and extrapyramidal syndromes. Moreover the compounds of the present invention perform a modulatory action on the immune system and, particularly, an inhibitory action on the secretion of TNF (tumor necrosis factor). They can therefore be favorably used in the therapy of pathologies characterized by a modified immunological reactivity and/or by autoimmunological symptoms like multiple sclerosis, cachectic situations associated with infections and neoplastic diseases, pulmonary fibrosis, rheumatoid arthritis, bacterial and protozoic infections, HIV (human immunodeficiency virus), cerebral complication of malaria, insulin dependent diabetes and several pathologies linked to organ transplantation or allergy caused pathologies.

Another object of the invention is directed to the use of phosphoryl-L-serine-N-acyl-sphinogosine of the formula I or II as defined above, in the preparation of pharmaceutical compositions to be employed in the treatment of diseases or conditions as explained above.

Another object of the present invention relates to pharmaceutical preparations containing phosphoryl-L-serine-N-acyl-sphingosine of formula I as active ingredient, optionally together with usual pharmaceutical excipients to be administered to a patient in need thereof. These pharmaceutical preparations can be for oral, rectal, parenteral, local or transdermic use. The pharmaceutical preparations can be presented in solid or semisolid form, e.g. as pills, tablets, gelatine covered capsules, or soft gelatine capsules. For the parenteral use it is possible to use formulations for intramuscular, subcutaneous or transdermic use, or formulations suitable for infusions or intravenous injections, and they can therefore be prepared as solutions of active components or as a lyophilized powder of the active components, eventually to be added to one or more excipients or pharmaceutically acceptable solvents, which are usable for the aforesaid purpose and osmolar with physiological fluids. For the local application spray preparations, e.g. nasal sprays, can be considered, or ointments for topical use, or plasters for transdermal administration. The preparations of the invention can be used both in humans and animals. They contain preferably between 0.01% and 10% of the active components for solutions, sprays, ointments and creams, and between 1% and 100%, preferably between 5% and 50% of the active component, for the solid form preparation, the remaining being made up of excipients. The dosage will be determined according to the indication, the desired effect and the route of administration. The daily dosage for the injectable (subcataneous or intramuscular) or transdermic or oral administration in humans of phosphoryl-L-serine-N-acyl-sphingosine of formula I varies between 0.5 and 12 mg/kg body weight of active substance.

Phosphoryl-L-serine-N-acyl-sphingosine, as described by formulae I or II, is a derivative of the natural compound sphingomyelin and, concerning the N-acyl-sphingosine component, it is identical with the composition of the natural product, i.e., it is a mixture of different acylamino-alkenyl residues corresponding to the above mentioned formula, in which both n and R vary within the defined ranges, which are those of sphingomyelin. According to the starting material from which sphingomyelin is extracted, R can be a mixture of acyl residues belonging to palmitic, stearic, nervonic, lignoceric and, in minor amounts, to other acids of different saturated and unsaturated molecular species of the same order.

The present invention also concerns the corresponding compounds of formulae I and II in unitary composition, i.e. in which both n and R have a defined value within in the defined range. These compounds are novel. The compounds I and II can be prepared according to already known methods starting from an alcohol of formula III or of formula IV

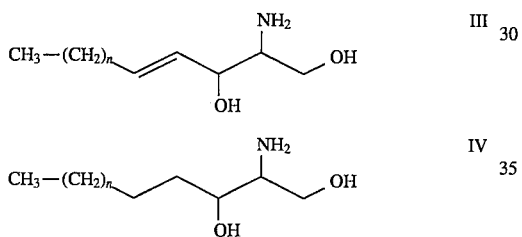

where n=6–16, which is reacted with phosphoric acid or a reactive derivative thereof, L-serine and a fatty acid R-COOH, where R has between 16 and 24 carbon atoms, in random sequence. The process involves acylating the amino-alcohol on the nitrogen atom with the mentioned acid and then reacting the obtained derivative with phosphoric acid and L-serine, or the steps can be carried out in different sequences. These new derivatives have the same pharmacological activities as reported for the product of formula I or II and can be used in therapy for the same indications. The following scheme shows a preferred sequence of the aforesaid preparation, which can also be used for the preparation of compounds of formula I or II

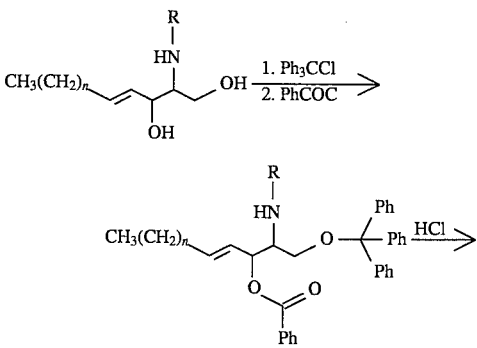

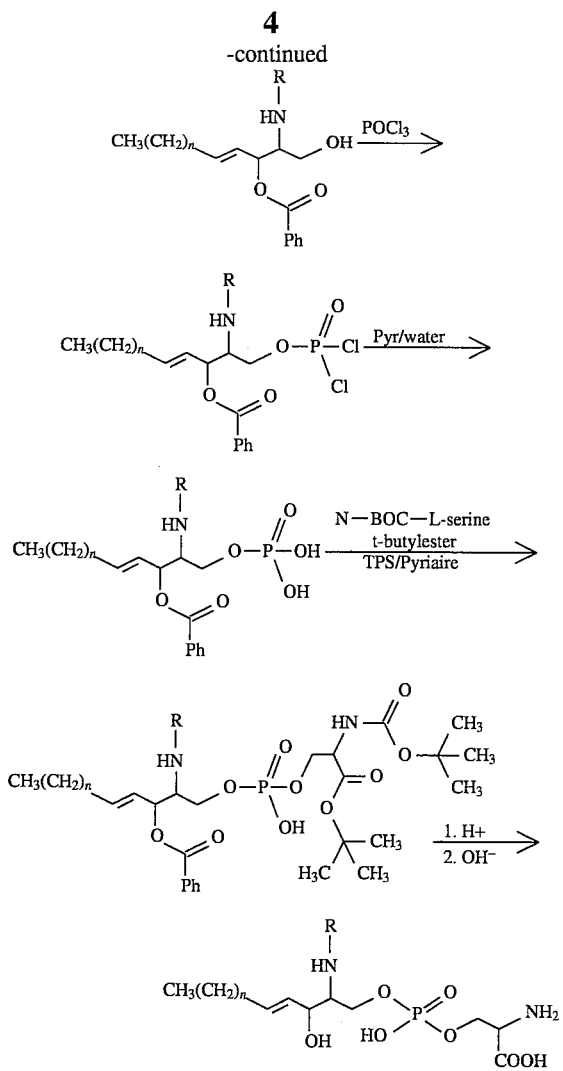

where Ph designates a phenyl group and TPS designates triisopropyl-benzenesulfonyl chloride. i.e. the N-acyl derivative of 4-doxyl-pentanoic acid of lyso-sphingomyelin. This process is, therefore, still another object of the present invention, and the resulting great technical advantage is clear. This procedure is illustrated in Ex. 1.

The starting materials for the preparation of phosphoryl-L-serine-N-acyl-sphingosine and the other analogous compounds are known or can be obtained according methods described in literature. The invention is illustrated in the following non-limiting Examples:

EXAMPLE 1

5 gr of chromatographically pure sphingomyelin were dissolved in a mixture of 80 ml of ethyl acetate and 80 ml of acetate buffer pH 5.6, 0.2M, $CaCl_2$ 0.04M saturated with serine. 320 U of phospholipase D from Streptomyces sp. were added and the reaction was conducted for 24 hours at 45° C. At the end 80 ml of chloroform/methanol 2:1 were added in order to extract the compound. After partitioning with 50 ml of HCl 0.5N, the organic layer was washed with 50 ml of water and then precipitated in 500 ml of ethanol containing 10 ml of sodium acetate 4.5M. The final purification was performed through chromatography on silica gel using a mixture of chloroform/methanol/water 60:30:3 as eluent. The pure fractions were gathered, concentrated and finally precipitated in 250 ml of acetone. Yield: 2.7

Phosphoryl-L-serine-N-acyl-sphingosine of formula I or II is generally present in the betaine form, i.e. according to formula

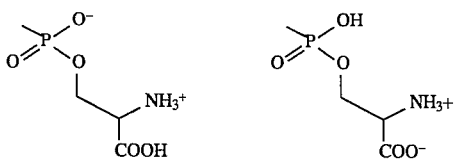

of the serine component, and that is also true for the aforesaid chemically unitary compound. If desired, also these betaines can be transformed into acid addition salts or basic salts, i.e. into alkaline, alkaline-earth or magnesium or heavy metal salts, or into salts of hydrohalogenic acids, as e.g. chlorides, bromides or iodides, in sulfates, sulfonates, or in organic acid salts. Also these salts, if therapeutically compatible can be used for therapeutic applications. Therapeutically non-acceptable salts are also part of the invention, and can optionally be used for the purification of the compounds. Compounds of formula I or II can be prepared by an already known procedure, e.g. according the aforesaid method and described in Biochemistry, vol. 28, No. 8, 1989, 3457.

It has now been found that the exchange between choline and serine can be done also directly utilizing phospholipase D, reacting sphingomyelin and serine, without the use of the above mentioned intermediate, gr. After thin layer chromatography on silica gel, the compound is ninhydrine and phosphorus positive having Rf =0.27 (sphingomyelin 0.20) and 0.11 (sphingomyelin 0.13) respectively, utilizing as eluent chloroform/methanol/water 60:30:4 and chloroform/ethyl acetate/n-propanol/methanol/ NH3 0.1N 25:25:25:22:13.

EXAMPLE 2

Pharmaceutical preparations in solution for injection

| Preparation No. 1 A vial of 2 ml contains: | |
| --- | --- |
| phosphoryl-L-serine-N-acyl-sphingosine | mg 5 |
| sodium chloride | mg 16 |
| citrate buffer pH 6 in distilled water, | ad 2 ml |
| Preparation No. 2 A vial of 2 ml contains: | |
| phosphoryl-L-serine-N-acyl-sphingosine | mg 50 |
| sodium chloride | mg 16 |
| citrate buffer pH 6 in distilled water, | ad 2 ml |
| Preparation No. 3 A flacon of 4 ml contains: | |
| phosphoryl-L-serine-N-acyl-sphingosine | mg 100 |
| sodium chloride | mg 32 |
| citrate buffer pH 6 in distilled water, | ad 4 ml |

The invention being described in this way, it is clear that these methods can be modified in several ways. These modifications cannot be considered different from the concept of the invention and all modifications, which can be considered as evident for an expert in the field, are included in the following claims.

We claim:

1. A pharmaceutical preparation containing a compound of formula I or II

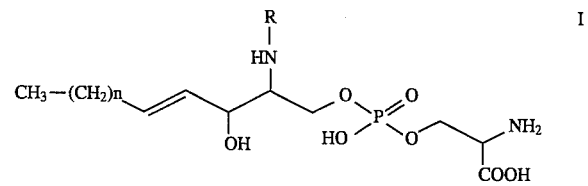

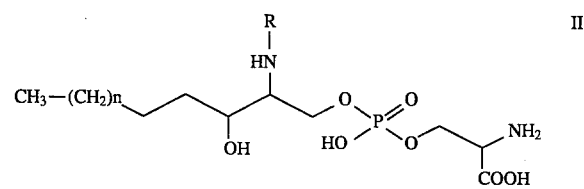

in which n is 6–16 and R means an acyl residue of a higher aliphatic acid having between 16 and 24 carbon atoms, the distribution of the values for n and R being those of a natural sphingomyelin, or a salt thereof as active ingredient together with a pharmacologically acceptable excipient.

2. A method for treating disorders of the nervous system or pathologies characterized by a modified immunological reactivity and/or symptoms of autoimmunity wherein phosphoryl-L-serine-N-acyl-spingosine formed by a mixture of compounds of formula I or II

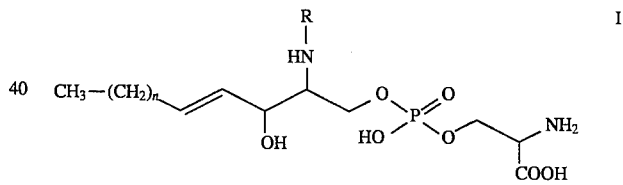

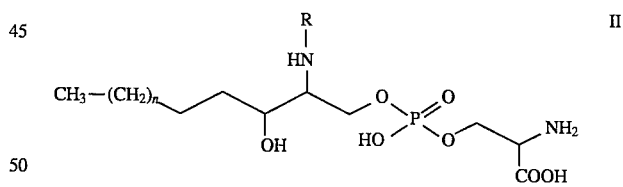

in which n is 6–16 and R means an acyl residue of a higher aliphatic acid having between 16 and 24 carbon atoms, the distribution of the values for n and R being those of a natural phingomyelin, or salts thereof is administered to a patient in need thereof.

3. A method for treating disorders of the nervous system or pathologies characterized by a modified immunological reactivity and/or symptoms of autoimmunity wherein compounds of formula I or II

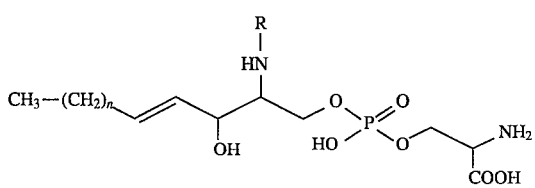

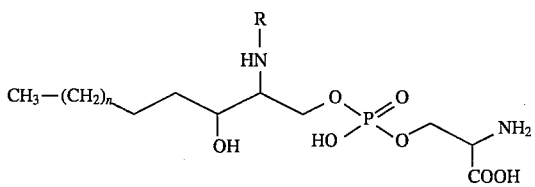

in which n is 6–16 and R is an acyl residue of a higher aliphatic acid having 16–24 carbon atoms, in chemically unitary form, is administered to a patient in need thereof.

4. A method of claims 2 or 3 wherein said disorder of the nervous system is the outcome of neuronal lesions or degenerations.

5. A method of claims 2 or 3 wherein said disorder or pathology is selected from the group consisting of ischemia, hypoxia, epilepsy, traumas or compressions, metabolic dysfunctions, toxic-infective diseases and neurodegenerative diseases.

6. A method of claims 2 or 3 wherein said disorder is selected from the group consisting of Alzheimer's, Parkinson's and Huntington's syndromes.

7. A method of claims 2 or 3 wherein said disorder or pathology is selected from the group consisting of psychometric involutive senile syndromes, chronic vascular cerebropathies of aging, senile dementia, pre-senile dementia following trauma, postanoxic cerebropathies and extrapyramidal syndromes.

8. A method of claims 2 or 3 wherein said disorder or pathology is selected from the group consisting of multiple sclerosis, cachectic situations associated with infections and neoplastic diseases, pulumonary fibrosis, rheumatoid arthritis, bacterial, protozoic and viral infections, cerebral complications of malaria and insulin dependent diabetes.

* * * * *